US008183024B2

(12) United States Patent

Cascao-Pereira et al.

(10) Patent No.: US 8,183,024 B2
(45) Date of Patent: May 22, 2012

(54) COMPOSITIONS AND METHODS COMPRISING A SUBTILISIN VARIANT

(75) Inventors: Luis G. Cascao-Pereira, Redwood City, CA (US); David A. Estell, San Francisco, CA (US); Frits Goedegebuur, Vlaardingen (NL); James T. Kellis, Jr., Woodside, CA (US); Ayrookaran J. Poulise, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 378 days.

(21) Appl. No.: 12/616,106

(22) Filed: Nov. 10, 2009

(65) Prior Publication Data

US 2010/0152087 A1 Jun. 17, 2010

Related U.S. Application Data

(60) Provisional application No. 61/113,552, filed on Nov. 11, 2008.

(51) Int. Cl.
*C12N 9/48* (2006.01)

(52) U.S. Cl. ........................................ 435/212; 510/392

(58) Field of Classification Search ........................ None
See application file for complete search history.

(56) References Cited

U.S. PATENT DOCUMENTS

| | | | |
|---|---|---|---|
| 4,246,612 | A | 1/1981 | Berry et al. |
| 4,430,243 | A | 2/1984 | Bragg |
| 4,435,307 | A | 3/1984 | Barbesgaard et al. |
| 4,515,705 | A | 5/1985 | Moeddel |
| 4,515,707 | A | 5/1985 | Brooks |
| 4,537,706 | A | 8/1985 | Severson, Jr. |
| 4,550,862 | A | 11/1985 | Barker et al. |
| 4,561,998 | A | 12/1985 | Wertz et al. |
| 4,597,898 | A | 7/1986 | Vander Meer |
| 4,683,195 | A | 7/1987 | Mullis et al. |
| 4,683,202 | A | 7/1987 | Mullis |
| 4,765,916 | A | 8/1988 | Ogar, Jr. et al. |
| 4,810,410 | A | 3/1989 | Diakun et al. |
| 4,965,188 | A | 10/1990 | Mullis et al. |
| 4,968,451 | A | 11/1990 | Scheibel et al. |
| 4,972,017 | A | 11/1990 | Smith et al. |
| 4,977,252 | A | 12/1990 | Chiu |
| 5,227,084 | A | 7/1993 | Martens et al. |
| RE34,606 | E | 5/1994 | Estell et al. |
| 5,340,735 | A | 8/1994 | Christianson et al. |
| 5,354,559 | A | 10/1994 | Morehouse |
| 5,486,303 | A | 1/1996 | Capeci et al. |
| 5,489,392 | A | 2/1996 | Capeci et al. |
| 5,500,364 | A | 3/1996 | Christianson et al. |
| 5,516,448 | A | 5/1996 | Capeci et al. |
| 5,565,145 | A | 10/1996 | Watson et al. |
| 5,565,422 | A | 10/1996 | Del Greco et al. |
| 5,569,645 | A | 10/1996 | Dinniwell et al. |
| 5,574,005 | A | 11/1996 | Welch et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,646,101 | A | 7/1997 | MacBeath |
| 5,686,014 | A | 11/1997 | Baillely et al. |
| 5,691,297 | A | 11/1997 | Nassano et al. |
| 5,695,679 | A | 12/1997 | Christie et al. |
| 5,698,504 | A | 12/1997 | Christie et al. |
| 5,700,676 | A | 12/1997 | Bott et al. |
| 5,705,464 | A | 1/1998 | Scheper et al. |
| 5,710,115 | A | 1/1998 | Patel et al. |
| 5,801,039 | A | 9/1998 | Maurer et al. |
| 5,855,625 | A | 1/1999 | Maurer et al. |
| 5,874,276 | A | 2/1999 | Fowler et al. |
| 5,879,584 | A | 3/1999 | Bianchetti et al. |
| 5,929,022 | A | 7/1999 | Velazquez |
| 5,935,826 | A | 8/1999 | Blue et al. |
| 5,955,340 | A | 9/1999 | Bott et al. |
| 6,225,464 | B1 | 5/2001 | Hiler, II et al. |
| 6,294,514 | B1 | 9/2001 | Welling |
| 6,306,812 | B1 | 10/2001 | Perkins et al. |
| 6,312,936 | B1 | 11/2001 | Poulose et al. |
| 6,326,348 | B1 | 12/2001 | Vinson et al. |
| 6,376,445 | B1 | 4/2002 | Bettiol et al. |
| 6,440,991 | B1 | 8/2002 | Zhu et al. |
| 6,482,628 | B1 | 11/2002 | Poulose et al. |
| 6,566,114 | B1 | 5/2003 | Kauppinen et al. |
| 6,602,842 | B2 | 8/2003 | Cuperus et al. |
| 6,605,458 | B1 | 8/2003 | Hansen et al. |
| 6,610,642 | B2 | 8/2003 | Ghosh et al. |
| 6,939,702 | B1 | 9/2005 | Vind et al. |
| 2006/0252155 | A1 | 11/2006 | Leeflang et al. |
| 2008/0090747 | A1 * | 4/2008 | Augustinus et al. .......... 510/392 |

FOREIGN PATENT DOCUMENTS

| | | | |
|---|---|---|---|
| EP | 0 214 761 | A2 | 3/1987 |
| EP | 0 218 272 | A1 | 4/1987 |
| EP | 0 238 023 | A2 | 9/1987 |
| EP | 0 258 068 | A2 | 3/1988 |
| EP | 0 305 216 | A1 | 3/1989 |
| EP | 0 331 376 | A2 | 9/1989 |
| EP | 0 495 257 | A1 | 7/1992 |

(Continued)

OTHER PUBLICATIONS

Bender, M.L. et al. "The Determination of the Concentration of Hydrolytic Enzyme Solutions: α-Chymotrypsin, Trypsin, Papain, Elastase, Subtilisin, and Acetylcholinesterase." *Journal of the American Chemical Society* 88(24):5890-5913, 1966. Chang, S. et al. "High frequency transformation of *Bacillus subtilis* protoplasts by plasmid DNA." *Mol. Gen. Genet* 168:111-115, 1979.

Dartois, V. et al. "Cloning, nucleotide sequence and expression in *Escherichia coli* of a lipase gene from *Bacillus subtilis* 168." *Biochimica et Biophysica Acta* 1131(3):253-260, 1992.

Ferrari, E. et al. "Genetics." in *Bacillus*, Biotechnology Handbooks, No. 2, ed. C.R. Harwood. New York: Plenum Press, pp. 57-72, 1989.

Haas, M.J. et al. "Cloning, expression and characterization of a cDNA encoding a lipase from *Rhizopus delemar*." *Gene* 109(1):107-113, 1991.

(Continued)

*Primary Examiner* — Christina Bradley
(74) *Attorney, Agent, or Firm* — Danisco US Inc.

(57) ABSTRACT

The present invention provides a subtilisin variant that is particularly well suited to cleaning applications. In particular, the present invention provides a *Bacillus* sp. subtilisin variant and cleaning compositions comprising this variant.

22 Claims, No Drawings

FOREIGN PATENT DOCUMENTS

| | | | |
|---|---|---|---|
| EP | 0 571 049 | A1 | 11/1993 |
| EP | 1 160 327 | A2 | 12/2001 |
| EP | 2 100 949 | A1 | 9/2009 |
| GB | 1296839 | A | 11/1972 |
| GB | 1372034 | A | 10/1974 |
| JP | 64-074992 | | 3/1989 |
| WO | WO 88/09367 | A1 | 12/1988 |
| WO | WO 89/06270 | A1 | 7/1989 |
| WO | WO 90/09446 | A1 | 8/1990 |
| WO | WO 91/16422 | A1 | 10/1991 |
| WO | WO 92/21760 | A1 | 12/1992 |
| WO | WO 94/12621 | A1 | 6/1994 |
| WO | WO 94/26859 | A1 | 11/1994 |
| WO | WO 94/26860 | A1 | 11/1994 |
| WO | WO 95/01426 | A1 | 1/1995 |
| WO | WO 95/23221 | A1 | 8/1995 |
| WO | WO 97/11151 | A1 | 3/1997 |
| WO | WO 99/06521 | A1 | 2/1999 |
| WO | WO 99/34011 | A2 | 7/1999 |
| WO | WO 00/32601 | A2 | 6/2000 |
| WO | WO 02/14490 | A2 | 2/2002 |
| WO | WO 02/102955 | A1 | 12/2002 |
| WO | WO 2004/111178 | A1 | 12/2004 |
| WO | WO 2005/056782 | A2 | 6/2005 |
| WO | WO 2007/044993 | A2 | 4/2007 |
| WO | WO 2007/145964 | A2 | 12/2007 |
| WO | WO 2008/010925 | A2 | 1/2008 |

OTHER PUBLICATIONS

Hahn, J. et al. "Regulatory inputs for the synthesis of ComK, the competence transcription factor of *Bacillus subtilis*." *Molecular Microbiology* 21(4):763-775, 1996.

Kugimiya, W. et al. "Cloning and sequence analysis of cDNA encoding *Rhizopus niveus* lipase." *Bioscience, Biotechnology, and Biochemistry* 56(5):716-9, 1992.

Laemmli, U.K. "Cleavage of Structural Proteins during the Assembly of the Head of Bacteriophage T4." *Nature* 227(5259):680-685, 1970.

Neidhardt, F.C. et al. "Culture Medium for Enterobacteria." *J. Bacteriol.* 119(3):736-747, 1974.

Rawlings, N.D. et al. "MEROPS: the peptidase database." *Nucl. Acids Res.* 34(Suppl. 1):D270-272, 2006.

Sambrook, J. et al. "Splicing signals." In *Molecular Cloning: A Laboratory Manual*, 2nd ed. New York: Cold Spring Harbor Press, pp. 16.7-16.8, 1989.

Shimada, Y. et al. "cDNA Molecular Cloning of *Geotrichum candidum* Lipase." *J Biochem* 106(3):383-388, 1989.

Smith, M.D. et al. "Protoplast transformation in coryneform bacteria and introduction of an α-amylase gene from *Bacillus amyloliquefaciens* into Brevibacterium lactofermentum." *Appl. Enviro. Microbiol.* 51(3):634-639, 1986.

Yamaguchi, S. et al. "Cloning and structure of the mono- and diacylglycerol lipase-encoding gene from *Penicillium camembertii* U-150." *Gene* 103(1):61-7, 1991.

* cited by examiner

COMPOSITIONS AND METHODS COMPRISING A SUBTILISIN VARIANT

The present application claims priority to U.S. Provisional Patent Application Ser. No. 61/113,552, filed on Nov. 11, 2008, herein incorporated by reference.

FIELD OF THE INVENTION

The present invention provides a subtilisin variant that is particularly well suited to cleaning applications. In particular, the present invention provides a *Bacillus* sp. subtilisin variant and cleaning compositions comprising this variant.

BACKGROUND OF THE INVENTION

Typically, traditional domestic and industrial dishwashing compositions rely on a combination of high alkalinity detergent washes and chlorine bleach for cleaning and sanitizing dishware. Such systems generally perform well on bleachable stains. However, removal of protein-containing soils that are often present on dishware in homes, hospitals, cafeterias, and catering industries is problematic. In addition, very highly alkaline and chlorine-containing compositions are not considered to be consumer nor environmentally friendly.

Various attempts have been made to produce dishwashing compositions that are effective at removing proteinaceous soils. These compositions typically include proteases active under alkaline conditions (e.g., pH of at least 9.5). However, such compositions have significant drawbacks in that they are difficult to formulate in the liquid or gel forms commonly preferred by consumers for dishwashing detergents. In addition, alkaline dishwashing compositions are often considered to be irritants.

Some attempts have been made to produce low pH (e.g., pH less than 9.5) dishwashing compositions. These compositions are safer, more environmentally friendly and capable of formulation into gels and liquid forms. However, current low pH dishwashing compositions which have proven to be very ineffective at removing proteinaceous soils, even when high concentrations of enzymes (e.g., proteases) are formulated within the dishwashing compositions.

Thus, there remains a need in the art for dishwashing compositions that effectively remove proteinaceous soils from dishware. In addition, there remains a need for dishwashing compositions that are more environmentally and consumer friendly and are in a form that is easy to use and cost-effective.

Similarly there remains a need for fabric cleaning compositions that effectively remove proteinaceous soils from fabrics.

SUMMARY OF THE INVENTION

The present invention provides a *Bacillus* sp. subtilisin variant particularly suited for use in cleaning compositions. In addition, the present invention provides cleaning compositions comprising this subtilisin variant.

The present invention provides a subtilisin variant comprising the amino acid sequence set forth in SEQ ID NO:5. In some preferred embodiments, the present invention provides compositions comprising the subtilisin variant having the amino acid sequence set forth in SEQ ID NO:5. In some particularly preferred embodiments, the composition is a cleaning composition. In some preferred alternative embodiments, the cleaning compositions are laundry detergent, while in some other preferred embodiments, the cleaning compositions are dishwashing detergents. In some embodiments, the dishwashing detergents are automatic dishwashing detergents, while in other embodiments they are hand dishwashing detergents. In some preferred embodiments, the cleaning compositions are liquid detergents, while in some other embodiments, the cleaning compositions are gel, tablet, powder or granule detergents. In some embodiments, the cleaning compositions do not contain phosphate, while in some other embodiments, the cleaning compositions contain phosphate. In some preferred embodiments, the cleaning compositions further comprise at least one bleaching agent. In some yet further preferred embodiments, the cleaning compositions further comprise at least one additional enzyme. In some embodiments, the additional enzyme is/are selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

The present invention also provides methods for cleaning, comprising providing an item to be cleaned and a composition comprising the subtilisin variant set forth in SEQ ID NO:5, and contacting said item with said composition. In some further embodiments, the methods further comprise the step of rinsing said item to be cleaned. In some additional embodiments, the item is a dishware or fabric item. In some further embodiments, the methods further comprise the step of rinsing the dishware or fabric item.

DESCRIPTION OF THE INVENTION

The present invention provides a subtilisin variant particularly well suited to cleaning applications. In particular the present invention provides a *Bacillus* sp. subtilisin variant and cleaning compositions comprising the variant. The present invention further provides enzyme compositions have comparable or improved wash performance, as compared to presently used subtilisin proteases.

Unless otherwise indicated, the practice of the present invention involves conventional techniques commonly used in molecular biology, microbiology, protein purification, protein engineering, protein and DNA sequencing, recombinant DNA fields, and industrial enzyme use and development, all of which are within the skill of the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, definitions for a number of terms are provided below.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "compatible," means that the cleaning composition materials do not reduce the enzymatic activity of the protease enzyme(s) provided herein to such an extent that the protease is not effective as desired during normal use situations. Specific cleaning composition materials are exemplified in detail hereinafter.

As used herein, "effective amount of enzyme" refers to the quantity of enzyme necessary to achieve the enzymatic activity required in the specific application. Such effective amounts are readily ascertained by one of ordinary skill in the art and are based on many factors, such as the particular enzyme variant used, the cleaning application, the specific composition of the cleaning composition, and whether a liquid or dry (e.g., granular) composition is required, and the like.

As used herein, "having improved properties" used in connection with a "variant protease" refers to a protease variant with improved performance and/or improved stability with retained performance, relative to the corresponding wild-type protease. In some particularly preferred embodiments, the improved properties are selected from the group consisting of improved dishwash and/or laundry performance and improved stability, as well as the combination of improved dishwash and/or laundry performance and improved stability.

As used herein, the phrase "detergent stability" refers to the stability of a detergent composition. In some embodiments, the stability is assessed during the use of the detergent, while in other embodiments the term refers to the stability of a detergent composition during storage.

The term "improved stability" is used to indicate better stability of a variant protease in compositions during storage and/or better stability in the sud. In preferred embodiments, the variant protease exhibits improved stability in dish care and/or laundry detergents during storage and/or improved stability in the sud, which includes stability against oxidizing agents, sequestering agents, autolysis, surfactants and high alkalinity, relative to the corresponding wild-type enzyme.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$, peracids and other oxidants. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" and "thermostability" refer to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a variant when exposed to given temperature. However, it is not intended that the present invention be limited to any temperature stability level nor temperature range.

As used herein, the term "chemical stability" refers to the stability of a protein (e.g., an enzyme) towards chemicals that may adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the terms "purified" and "isolated" refer to the removal of contaminants from a sample. For example, an enzyme of interest is purified by removal of contaminating proteins and other compounds within a solution or preparation that are not the enzyme of interest. In some embodiments, recombinant enzymes of interest are expressed in bacterial or fungal host cells and these recombinant enzymes of interest are purified by the removal of other host cell constituents; the percent of recombinant enzyme of interest polypeptides is thereby increased in the sample.

As used herein, "protein of interest," refers to a protein (e.g., an enzyme or "enzyme of interest") which is being analyzed, identified and/or modified. Naturally-occurring, as well as recombinant (e.g., "mutant" or "variant") proteins find use in the present invention. As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably, as the plasmid is the most commonly used form of vector at present. However, the invention is intended to include such other forms of expression vectors that serve equivalent functions and which are, or become, known in the art.

In some preferred embodiments, the protease gene is ligated into an appropriate expression plasmid. The cloned protease gene is then used to transform or transfect a host cell in order to express the protease gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed by the host), and a transcription terminator that is exogenous or is supplied by the endogenous terminator region of the protease gene. In some embodiments, a selection gene such as an antibiotic resistance gene that enables continuous cultural maintenance of plasmid-infected host cells by growth in antimicrobial-containing media is also included.

The following cassette mutagenesis method may be used to facilitate the construction of the protease variant of the present invention, although other methods may be used. First, as described herein, a naturally-occurring gene encoding the protease is obtained and sequenced in whole or in part. Then, the sequence is scanned for a point at which it is desired to make a mutation (e.g., by deletion, insertion or substitution) of one or more amino acids in the encoded protease. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from about 10 to about 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site. Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide. As used herein, "corresponding region," generally refers to an analogous position along related proteins or a reference protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques. The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

As used herein, "equivalent residues" refers to proteins that share particular amino acid residues. For example, equivalent resides may be identified by determining homology at the level of tertiary structure for a protein (e.g., protease) whose tertiary structure has been determined by x-ray crystallography. Equivalent residues are defined as those for which the atomic coordinates of two or more of the main chain atoms of a particular amino acid residue of the protein having putative equivalent residues and the protein of interest are within about 0.13 nm and preferably about 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variant or expressing the desired protein variant. In the case of vectors which encode the pre- or prepro-form of the protein variant, such variant, when expressed, is typically secreted from the host cell into the host cell medium.

The term "introduced" in the context of inserting a nucleic acid sequence into a cell, means transformation, transduction or transfection. Means of transformation include, but are not limited, to any suitable methods known in the art, such as protoplast transformation, calcium chloride precipitation, electroporation, naked DNA and the like, as known in the art. (See e.g., Chang and Cohen, Mol Gen Genet, 168:111-115, 1979; Smith et al., Appl Env Microbiol, 51:634, 1986; and Ferrari et al, in Harwood, *Bacillus*. Plenum Publishing Corporation, pp. 57-72, 1989).

The term "promoter/enhancer" denotes a segment of DNA which contains sequences capable of providing both promoter and enhancer functions. The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (See e.g., Sambrook et al., Molecular Cloning: A Laboratory Manual, 2nd ed., Cold Spring Harbor Laboratory Press, New York, pp. 16.7-16.8, 1989).

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the terms "amplifiable marker," "amplifiable gene," and "amplification vector" refer to a marker, gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to amplification methods (e.g., the polymerase chain reaction), refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the terms "polymerase chain reaction" and "PCR" refer to the methods of U.S. Pat. Nos. 4,683,195, 4,683,202, and 4,965,188, which include methods for increasing the concentration of a segment of a target sequence in a mixture of genomic DNA without cloning or purification. These methods are well-known to those in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "cleaning composition" refers to any composition that finds use in cleaning applications. It is intended that the term encompass (unless otherwise indicated), granular or powder all-purpose or "heavy-duty" washing agents (e.g., laundry detergents), liquid, gel, or paste all-purpose washing agents (e.g., "heavy-duty liquid" detergents), liquid and powder fine-fabric detergents, hand dishwashing agents, light duty dishwashing agents (e.g., high-foaming detergents), machine dishwashing agents (i.e., "automatic dishwashing detergents") including tablet, granular, liquid detergents, rinse-aid detergents for household and institutional use, liquid cleaning and disinfecting agents (e.g., antibacterial hand soaps), laundry bars, mouthwashes, denture cleaners, car shampoo, carpet shampoo, bathroom cleaners, hair shampoos for humans and other animals, hair rinses for humans and other animals, shower gels, bath gels, foam baths and metal cleaners, and cleaning auxiliaries (e.g., bleach additives, laundry additives, pre-treatment compositions, including "stain stick" and other pre-treatment formats).

As used herein, the terms "detergent composition" and "detergent formulation" are used in reference to mixtures which are intended for use in a wash medium for the cleaning of soiled objects. In preferred embodiments, the term is used in reference to detergents used to clean laundry, dishes, cutlery, etc. (e.g., "dishwashing detergents"). It is not intended that the present invention be limited to any particular detergent formulation or composition. Indeed, it is intended that in addition to detergents that contain at least one protease of the present invention, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "dishwashing composition" refers to all forms of compositions for cleaning dishware, including cutlery, including but not limited to powder, tablet, gel, granular and liquid forms. It is not intended that the present invention be limited to any particular type of dishware composition. Indeed, the present invention finds use in cleaning dishware (e.g., dishes, including, but not limited to plates, cups, glasses, bowls, etc.) and cutlery (e.g., utensils, including but not limited to spoons, knives, forks, serving utensils, etc.) of any material, including but not limited to ceramics, plastics, metals, china, glass, acrylics, etc. The term "dishware" is used herein in reference to both dishes and cutlery.

The term "relevant washing conditions" is used herein to indicate the conditions, particularly washing temperature, time, washing mechanics, sud concentration, type of detergent and water hardness, actually used in households in a dish or fabric detergent market segment.

The term "improved wash performance" is used to indicate that a better end result is obtained in stain removal from dishware, cutlery or fabrics under relevant washing conditions, or that less mutant protease, on weight basis, is needed to obtain the same end result relative to the corresponding wild-type enzyme.

The term "retained wash performance" is used to indicate that the wash performance of a mutant protease enzyme, on weight basis, is at least about 80% relative to the corresponding wild-type protease under relevant washing conditions.

Wash performance of proteases is conveniently measured by their ability to remove certain representative stains under appropriate test conditions. In these test systems, other relevant factors, such as detergent composition, sud concentration, water hardness, washing mechanics, time, pH, and/or temperature, can be controlled in such a way that conditions typical for household application in a certain market segment (e.g., dishwashing, fabric cleaning, etc.) are imitated. The laboratory application test system described herein is representative for household application when used on proteolytic enzymes modified through DNA mutagenesis. Thus, the methods provided herein facilitate the testing of large amounts of different enzymes and the selection of those enzymes which are particularly suitable for a specific type of detergent application. In this way "tailor made" enzymes for specific application conditions are easily selected.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid, gel or dry (e.g., granular, bar) composition is required, etc.

The term "cleaning adjunct materials" as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

As used herein, a "low detergent concentration" system includes detergents where less than about 800 ppm of detergent components are present in the wash water. Japanese detergents are typically considered low detergent concentration systems, as they usually have approximately 667 ppm of detergent components present in the wash water.

As used herein, a "medium detergent concentration" system includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" system includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions," "laundry cleaning composition," and "laundry detergent" refer to composition for cleaning soiled clothing and/or fabric. It is intended that any form, including powder, tablet, gel, granular and liquid forms be encompassed by the present invention. It is not intended that the present invention be limited to any particular type of clothing and/or fabric. These terms encompass hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile surface cleaning compositions, including but not limited to dishwashing detergent compositions, oral cleaning compositions, denture cleaning compositions, and personal cleansing compositions.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "subtilisin" refers any member of the S8 serine protease family as described in MEROPS—The Peptidase Data base (Rawlings et al., MEROPS: the peptidase database, Nucl Acids Res, 34 Database issue, D270-272, 2006).

Suitable host strains for production of the variant protease provided herein include transformable microorganisms in which expression of the protease can be achieved. Specifically host strains of the same species or genus from which the protease is derived, are suitable, such as a *Bacillus* strain, preferably an alkalophilic *Bacillus* strain and most preferably *Bacillus nov.* spec. PB92 or a mutant thereof, having substantially the same properties. Also, *B. subtilis, B. licheniformis* and *B. amyloliquefaciens* strains are among the preferred strains. Other suitable and preferred host strains include those strains which are substantially incapable of producing extracellular proteolytic enzymes prior to the transformation with a mutant gene. Of particular interest are protease deficient *Bacillus* host strains, such as a protease deficient derivative of *Bacillus nov.* spec. PB92. Expression of the proteases is obtained by using expression signals that function in the selected host organism. Expression signals include sequences of DNA regulating transcription and translation of the protease genes. Proper vectors are able to replicate at sufficiently high copy numbers in the host strain of choice or enable stable maintenance of the protease gene in the host strain by chromosomal integration.

The variant proteolytic enzyme (i.e., variant protease) according to the invention is prepared by cultivating, under appropriate fermentation conditions, a transformed host strain comprising the desired mutant proteolytic gene or genes, and recovering the produced enzymes. Preferably, the protease being expressed is secreted into the culture medium, which facilitates its recovery, or in the case of gram negative bacterial host strains into the periplasmic space. For secretion a suitable amino terminal signal sequence is employed, preferably the signal sequence encoded by the original gene if this is functional in the host strain of choice.

In some embodiments, several substitutions are combined, in order to increase the stability and/or performance of a subtilisin in detergent compositions. Thus, the present invention provides the following protease variant that provides improved wash performance (e.g., PB92 variant having N76D+N87R+G118R+S128L+P129Q+S130A+S188D+N248R; using BPN' numbering; "PX3"). This variant is referred to herein as a "subtilisin protease variant," "mutant protease," "variant protease," "protease variant," "*Bacillus* sp. protease," "*Bacillus* sp. subtilisin variant," and "mutant protease variant." The amino acid sequence of this variant is set forth in SEQ ID NO:5.

Accordingly, the present invention provides this subtilisin variant, suitable for use in detergent composition(s) and/or in washing process(es). It is to be understood that positions homologous to amino acid positions of the PB92 reference subtilisin (and numbered according to an alignment with BPN') will fall under the scope of the claims.

Cleaning Compositions

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease separated (i.e., not in contact with each other) until combination of the two components is appropriate are used. Such separation methods include any suitable method known in the art (e.g., gelcaps, encapsulation, tablets, physical separation, etc.).

The serine protease variant of the present invention is useful in formulating various detergent compositions. The cleaning composition of the present invention may be advantageously employed for example, in laundry applications, hard surface cleaning, automatic dishwashing applications, as well as cosmetic applications such as dentures, teeth, hair and skin.

The variant protease of the present invention finds use in granular, powder, gel, and liquid compositions.

The protease variant of the present invention also finds use in cleaning additive products. A cleaning additive product including the variant protease of the present invention is ideally suited for inclusion in a wash process when additional bleaching effectiveness is desired. Such instances include, but are not limited to low temperature solution cleaning applications. The additive product may be, in its simplest form, the protease variant as provided by the present invention. In some embodiments, the additive is packaged in dosage form for addition to a cleaning process where a source of peroxygen is employed and increased bleaching effectiveness is desired. In some embodiments, the single dosage form comprises a pill, tablet, gelcap or other single dosage unit including pre-measured powders and/or liquids. In some embodiments, filler and/or carrier material(s) are included, in order to increase the volume of such composition. Suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol. In some embodiments, the compositions comprise from about 5% to about 90% of such materials. In additional embodiments, acidic fillers are used to reduce the pH of the composition. In some alternative embodiments the cleaning additive includes at least one activated peroxygen source as described below and/or adjunct ingredients as more fully described below.

The cleaning compositions and cleaning additives of the present invention require an effective amount of serine protease enzyme as provided in the present invention. In some embodiments, the required level of enzyme is achieved by the addition of the serine protease variant provided by the present invention. Typically, the cleaning compositions of the present invention comprise at least 0.0001 weight percent, from about 0.0001 to about 10, from about 0.001 to about 1, or even from about 0.01 to about 0.1 weight percent of at least one serine protease provided by the present invention.

In some preferred embodiments, the cleaning compositions provided herein are typically formulated such that, during use in aqueous cleaning operations, the wash water has a pH of from about 5.0 to about 11.5, or in alternative embodiments, even from about 6.0 to about 10.5. In some preferred embodiments, liquid product formulations are typically formulated to have a neat pH from about 3.0 to about 9.0, while in some alternative embodiments the formulation has a neat pH from about 3 to about 5. In some preferred embodiments, granular laundry products are typically formulated to have a pH from about 8 to about 11. Techniques for controlling pH at recommended usage levels include the use of buffers, alkalis, acids, etc., and are well known to those skilled in the art.

In some particularly preferred embodiments, when the variant protease is employed in a granular composition or liquid, the variant protease is in the form of an encapsulated particle to protect the enzyme from other components of the granular composition during storage. In addition, encapsulation also provides a means of controlling the availability of the serine protease during the cleaning process and may enhance performance of the serine protease. It is contemplated that the encapsulated serine protease of the present invention will find use in various settings. It is also intended that the serine protease be encapsulated using any suitable encapsulating material(s) and method(s) known in the art.

In some preferred embodiments, the encapsulating material typically encapsulates at least part of the serine protease catalyst. In some embodiments, the encapsulating material is water-soluble and/or water-dispersible. In some additional embodiments, the encapsulating material has a glass transition temperature of 0° C. or higher (See e.g., WO 97/11151, particularly from page 6, line 25 to page 7, line 2, for more information regarding glass transition temperatures).

In some embodiments, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. In some embodiments in which the encapsulating material is a carbohydrate, it is selected from the group consisting of monosaccharides, oligosaccharides, polysaccharides, and combinations thereof. In some preferred embodiments, the encapsulating material is a starch (See e.g., EP 0 922 499; and U.S. Pat. Nos. 4,977,252, 5,354,559, 5,935,826, for descriptions of some exemplary suitable starches).

In additional embodiments, the encapsulating material comprises a microsphere made from plastic (e.g., thermoplastics, acrylonitrile, methacrylonitrile, polyacrylonitrile, polymethacrylonitrile and mixtures thereof; commercially available micro spheres that find use include, but are not limited to EXPANCEL® (Casco Products, Stockholm, Sweden), PM 6545, PM 6550, PM 7220, PM 7228, EXTENDOSPHERES®, and Q-CEL® (PQ Corp., Valley Forge, Pa.), LUXSIL® and SPHERICEL1® (Potters Industries, Inc., Carlstadt, N.J. and Valley Forge, Pa.).

As described herein, in some embodiments, the variant protease of the present invention finds use in laundry detergents. These applications place enzymes under various environmental stresses. The variant protease of the present invention provides advantages over many currently used enzymes, due to its stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, a European detergent typically has about 4500-5000 ppm of detergent components in the wash water, while a Japanese detergent typically has approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between 10 and 30° C. (e.g., about 20° C.), whereas the temperature of wash water in Europe is typically between 30 and 60° C. (e.g., about 40° C.). In addition, in some further regions, cold water is typically used for laundry, as well as dish washing applications. In some embodiments, the "cold water washing" of the present invention utilizes washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | Greater than 10.5 | greater than 180 |

European water hardness is typically greater than 10.5 (for example 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, usually less than 4, for example 3 grains per gallon mixed $Ca^{2+}/Mg^{2+}$.

Accordingly, in some embodiments, the present invention provides a variant protease that provides surprising wash performance in at least one set of wash conditions (e.g., water temperature, water hardness, and/or detergent concentration). In some embodiments, the variant protease of the present invention is comparable in wash performance to other subtilisin proteases. In some embodiments, the variant protease of the present invention exhibits enhanced wash performance as compared to subtilisin proteases that are currently commercially available. Thus, in some preferred embodiments of the present invention, the variant protease provided herein exhibits enhanced oxidative stability, enhanced thermal stability, and/or enhanced chelator stability. In addition, the variant protease of the present invention finds use in cleaning compositions that do not include detergent ingredients, again either alone or in combination with builders and stabilizers.

In some embodiments of the present invention, the cleaning compositions comprise the variant protease of the present invention at a level from about 0.00001% to about 10% by weight of the composition and the balance (e.g., about 99.999% to about 90.0%) comprising cleaning adjunct materials by weight of composition. In other aspects of the present invention, the cleaning compositions of the present invention comprise the variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

As described further herein, in some embodiments, preferred cleaning compositions comprise one or more additional enzymes or enzyme derivatives which provide cleaning performance and/or fabric care benefits, in addition to the protease variant provided herein.

Processes of Making and Using Cleaning Compositions

In some preferred embodiments compositions of the present invention are formulated into any suitable form and prepared by any process chosen by the formulator (See e.g., U.S. Pat. Nos. 5,879,584, 5,691,297, 5,574,005, 5,569,645, 5,565,422, 5,516,448, 5,489,392, and 5,486,303, for some non-limiting examples). In some embodiments in which a low pH cleaning composition is desired, the pH of such composition is adjusted via the addition of an acidic material such as HCl.

Adjunct Materials

While not essential for the purposes of the present invention, in some embodiments, the non-limiting list of adjuncts described herein are suitable for use in the cleaning compositions of the present invention. Indeed, in some embodiments, adjuncts are incorporated into the cleaning compositions of the present invention. In some embodiments, adjunct materials assist and/or enhance cleaning performance, treat the substrate to be cleaned, and/or modify the aesthetics of the cleaning composition (e.g., perfumes, colorants, dyes, etc.). It is understood that such adjuncts are in addition to the serine protease variant of the present invention. The precise nature of these additional components, and levels of incorporation thereof, depends on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to those provided explicitly herein, additional examples are known in the art (See e.g., U.S. Pat. Nos. 5,576,282, 6,306,812 and 6,326,348). In some embodiments, the aforementioned adjunct ingredients constitute the balance of the cleaning compositions of the present invention.

Surfactants

In some embodiments, the cleaning compositions of the present invention comprise at least one surfactant or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

Builders

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

Chelating Agents

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

Deposition Aids

In some embodiments, the cleaning compositions of the present invention include at least one deposition aid. Suitable deposition aids include, but are not limited to polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

Anti-Redeposition Agents

As indicated herein, anti-redeposition agents find use in some embodiments of the present invention. In some preferred embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some preferred embodiments, the anti-redeposition agent is a non-ionic surfactant as known in the art (See e.g., EP 2 100 949).

Dye Transfer Inhibiting Agents

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

Silicates

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some preferred embodiments, silicates are present at a level of from about 5% to about 15% by weight of the composition.

Dispersants

In some embodiments, the cleaning compositions of the present invention contain at least one dispersant. Suitable water-soluble organic materials include, but are not limited to the homo- or co-polymeric acids or their salts, in which the polycarboxylic acid comprises at least two carboxyl radicals separated from each other by not more than two carbon atoms.

Enzymes

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

Any other suitable protease finds use in the compositions of the present invention. Suitable proteases include those of animal, vegetable or microbial origin. In some particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease described in WO 89/06270. Preferred commercially available protease enzymes include MAXATASE®, MAXACAL™ MAXAPEM™, OPTICLEAN®, OPTIMASE®, PROPERASE®, PURAFECT®, PURAFECT® OXP, PURAMAX®, PURAFAST™, and EXCELLASE™ (Genencor); ALCALASE®, SAVINASE®, PRIMASE®, DURAZYM™, KANNASE®, POLARZYME®, LIQUANASE®, OVOZYME€„ NEUTRASE€„ RELASE® and ESPERASE® (Novozymes); and BLAP™ (Henkel Kommanditgesellschaft auf Aktien, Duesseldorf, Germany. Various proteases are described in WO95/23221, WO 92/21760, and U.S. Pat. Nos. 5,801,039, 5,340,735, 5,500,364, 5,855,625, U.S. Pat. Nos. RE 34,606, 5,955,340, 5,700,676, 6,312,936, and 6,482,628, and various other patents. In some further embodiments, metalloproteases find use in the present invention, including but not limited to the neutral metalloprotease described in WO 07/044993.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, EP 305 216, and U.S. Pat. No. 6,939,702), *Rhizomucor miehei* lipase (See e.g., EP 238 023), *Candida* lipase, such as *C. antarctica* lipase (e.g., the *C. antarctica* lipase A or B; See e.g., EP 214 761), a *Pseudomonas* lipase such as *P. alcaligenes* and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In other aspects of the present invention, the cleaning compositions of the present invention also comprise, lipases at a level of about 0.0001% to about 10%, about 0.001% to about 5%, about 0.001% to about 2%, about 0.005% to about 0.5% lipase by weight of the composition.

Any amylase (alpha and/or beta) suitable for use in alkaline solutions also find use in some embodiments of the present invention. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL®, STAINZYME®, STAINZYME PLUS®, STAINZYME ULTRA®, NATALASE®, and BAN™ (Novozymes), as well as POWERASE™, RAPIDASE®, and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In other aspects of the present invention, the cleaning compositions of the present invention also comprise, amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). In some embodiments, the cleaning compositions of the present invention further comprise cellulases at a level from about 0.00001% to about 10% of additional cellulase by weight of the composition and the balance of cleaning adjunct materials by weight of composition. In other aspects of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. No. 6,566,114, U.S. Pat. No. 6,602,842, and U.S. Pat. No. 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In other aspects of the present invention, the cleaning compositions of the present invention also comprise, mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In other aspects of the present invention, the cleaning compositions of the present invention also comprise peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Enzyme Stabilizers

In some embodiments of the present invention, the enzymes used in the detergent formulations of the present invention are stabilized. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

Bleach, Bleach Activators and Bleach Catalysts

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphaic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

Catalytic Metal Complexes

In some embodiments, the cleaning compositions of the present invention contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO 2000/32601, and U.S. Pat. No. 6,225,464).

Metal Care Agents

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent(s).

Processes of Making and Using Cleaning Compositions

The cleaning compositions of the present invention are formulated into any suitable form and prepared by any suitable process chosen by the formulator, (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats).

Method of Use

In preferred embodiments, the cleaning compositions of the present invention find use in cleaning surfaces (e.g., dishware) and/or fabrics. In some embodiments, at least a portion of the surface and/or fabric is contacted with at least one embodiment of the cleaning compositions of the present invention, in neat form or diluted in a wash liquor, and then the surface and/or fabric is optionally washed and/or rinsed. For purposes of the present invention, "washing" includes, but is not limited to, scrubbing, and mechanical agitation. In some embodiments, the fabric comprises any fabric capable of being laundered in normal consumer use conditions. In preferred embodiments, the cleaning compositions of the present invention are used at concentrations of from about 500 ppm to about 15,000 ppm in solution. In some embodiments in which the wash solvent is water, the water temperature typically ranges from about 5° C. to about 90° C. In some preferred embodiments for fabric cleaning, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ppm (parts per million); M (molar); mM (millimolar); μm (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); w/v (weight to volume); v/v (volume to volume); g (gravity); OD (optical density); aa (amino acid); by (base pair); kb (kilobase pair); kD (kilodaltons); suc-AAPF-pNA (succinyl-L-alanyl-L-alanyl-L-prolyl-L-phenyl-alanyl-para-nitroanilide); BPN' (*Bacillus amyloliquefaciens* subtilisin); DMSO (dimethyl sulfoxide); cDNA (copy or complementary DNA); DNA (deoxyribonucleic acid); ssDNA (single stranded DNA); dsDNA (double stranded DNA); dNTP (deoxyribonucleotide triphosphate); DTT (1,4-dithio-DL-threitol); H2O (water); dH2O (deionized water); HCl (hydrochloric acid); MgCl2 (magnesium chloride); MOPS (3-[N-morpholino]propanesulfonic acid); NaCl (sodium chloride); PAGE (polyacrylamide gel electrophoresis); PB92 (*Bacillus clausii* subtilisin); PBS (phosphate buffered saline [150 mM NaCl, 10 mM sodium phosphate buffer, pH 7.2]); PEG (polyethylene glycol); PCR (polymerase chain reaction); PMSF (phenylmethylsulfonyl fluoride); RNA (ribonucleic acid); SDS (sodium dodecyl sulfate); Tris (tris(hydroxymethyl) aminomethane); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l KH2PO4, and 12.54 g/l K2HPO4); OD280 (optical density at 280 nm); OD600 (optical density at 600 nm); A405 (absorbance at 405 nm); Vmax (the maximum initial velocity of an enzyme catalyzed reaction); HEPES (N-[2-Hydroxyethyl]piperazine-N-[2-ethanesulfonic acid]); Tris-HCl (tris[Hydroxymethyl]aminomethane-hydrochloride); TCA (trichloroacetic acid); HPLC (high pressure liquid chromatography); RP-HPLC (reverse phase high pressure liquid chromatography); TLC (thin layer chromatography); Taq (Thermus aquaticus DNA polymerase); Klenow (DNA polymerase I large (Klenow) fragment); EDTA (ethylenediaminetetracetic acid); EtOH (ethanol); SDS (sodium dodecyl sulfate); Tris (tris(hydroxymethyl)aminomethane); TAED (N,N,N'N'-tetraacetylethylenediamine); PI (performance index); SR (soil or stain removal); MS (mass spectroscopy); AATCC (American Association of Textile and Coloring Chemists); Arzberg (Arzberg-Porzellan GmbH, Schirnding, Germany); BASF (BASF Corp., Florham Park, N.J.); BioRad (BioRad, Richmond, Calif.); Cognis (Cognis Corp, USA, Cincinnati, Ohio); Finnzymes (Finnzymes Oy, Espoo, Finland); Henkel (Henkel, GmbH, Dusseldorf, Germany); IKW (Industrieverband Kβrperflege and Waschmittel, =The German Cosmetic, Toiletry, Perfumery and Detergent Association, Frankfurt, Germany); Invitrogen (Invitrogen Corp., Carlsbad, Calif.); Kontron (Kontron Instruments, Zurich, Switzerland); Macherey-Nagel (Macherey-Nagel, Easton, Pa.); Miele (Miele, Princeton, N.J.) Merieux (Instirut Merieux, Codex, FR); QIAGEN® (QIAGEN®, Inc., Valencia, Calif.); (Reckitt Benckiser, Berks, United Kingdom); Sigma (Sigma Chemical Co., St. Louis, Mo.); Sorvall (Sorvall Instruments, a subsidiary of DuPont Co., Biotechnology Systems, Wilmington, Del.); and wfk Testmaterials (Testgewebe GmbH, Bruggen-Bracht, Germany).

Example 1

Construction of the Subtilisin Variant

As described herein, the subtilisin variant was prepared by fusion PCR as known in the art (See e.g., US Pat. Appln. Publn. No. 2006/0252155. Table 1-1 provides the sequences of the primers used for fusion PCR.

TABLE 1-1

Primers Used In Fusion PCR*

| Primer Sequence | Primer Name |
|---|---|
| CGGGACGATTGCTGCTTTA**GAC**AATTCGATTGGCGTTC (SEQ ID NO: 1) | N76D-Fw |
| GAACGCCAATCGAATT**GTC**TAAAGCAGCAATCGTCCCG (SEQ ID NO: 2) | N76D-Rv |
| GCAATTC**AGATCT**TCCTTCAGGTTATGACC (SEQ ID NO: 3) | pHPLT-BglII-Fw |
| GCATCGA**AGATCT**GATTGCTTAACTGCTTC (SEQ ID NO: 4) | pHPLT-BglII-Rv |

*The codon for generation of a substitution at position 76, and the restriction enzyme sites are shown in bold.

A DNA template of a *B. clausii* PB92 variant (containing the following substitutions N87R+G118R+S128L+P129Q+S130A+S188D+N248R; using BPN' numbering, and designated herein as GCI-P039) was used to generate a subtilisin variant further comprising a N76D substitution (designated herein as “PX3”). A variant having an identical amino acid sequence to PX3 can also be produced from a DNA template of a *B. lentus* GG36 variant (containing the following substitutions S87R+G118R+S128L+P129Q+S130A+S188D+N248R; using BPN' numbering) by introduction of a N76D substitution.

The BglII-Fw primer was combined with N76D-Rv in the first reaction to generate the first fragment and the second fragment was prepared by combining the BglII-Rv primer with the N76D-Fw primer in a second reaction. PHUSION™ polymerase (Finnzymes) was used in the PCR reactions. In these experiments, 2 μl of 10 mM forward and reverse primers, 1 μl 10 mM dNTPs, 10 μl 5×HF Phusion buffer, 1.5 μl DMSO, 1 unit polymerase, and 1 μl template was added to a volume of 50 μl. The following PCR program was used: 3 min denaturation at 95° C., 1 min annealing at 65° C., and 1 min, 15 sec elongation at 72° C., for 30 cycles, followed by 7 min at 72° C. Upon completion, the reaction products were stored at room temperature.

DNA fragments of the expected sizes from the two PCR reactions were purified from agarose gels using PCR purification columns (Macherey-Nagel). The two desired fragments were fused by PCR amplification using the BglII forward and reverse primers and PHUSION™ polymerase, using the following program: 3 min denaturation at 95° C., 1 min annealing at 65° C., and 2 min elongation at 72° C. for 25 cycles, followed by 7 min at 72° C. Upon completion, the reaction products were stored at room temperature.

DNA fragments from the fusion PCR reaction were obtained by digestion with BglII restriction enzyme and purified from agarose gels. The DNA fragments were subsequently ligated with BglII digested pHPLT plasmid backbone with 1 μl T4 DNA ligase, 8 μl 5×T4 ligation buffer in a final volume of 40 μl, overnight at 14° C.

Competent *B. subtilis* cells (phenotype: ΔaprE, ΔnprE, oppA, ΔspoIIE, degUHy32, ΔamyE::[xylR,pxylA-comK]) were transformed using 10 μl of the ligation product to obtain protease positive transformants as known in the art (See e.g., WO 02/14490). The bacteria were made competent by the induction of the comK gene under control of a xylose inducible promoter (See e.g., Hahn et al., Mol Microbiol, 21:763-775, 1996). Protease positive clones were selected on skim milk/agar plates, isolated, sequenced and protein was produced in shaker flask cultures to generate significant quantities of enzyme samples for characterization.

Example 2

Production of the Subtilisin Variant in *Bacillus subtilis*

The subtilisin variant was produced by growing the *B. subtilis* transformants overnight at 37° C. in 10 ml TSB (tryptone and soy based broth) medium. A 250 μl aliquot of the overnight culture was transferred into 25 ml of a MOPS based defined medium in a 100 ml shake flask and grown at 37° C. for 68 hours. The defined medium was made essentially as known in the art (See, Neidhardt et al., J Bacteriol, 119: 736-747, 1974), except that $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The protease of interest (i.e., the protease variant) was isolated from the culture medium.

Example 3

Analytical Methods to Determine the Purity of the Subtilisin Variant

In this Example, methods used to determine the purity of the recombinant subtilisin obtained from *B. subtilis* cultures are described. The protease was considered pure when a single band or peak was found by gel electrophoresis and high performance liquid chromatography (HPLC), respectively.

Polyacrylamide gel electrophoresis (PAGE) in the presence of sodium dodecyl sulphate (SDS) was conducted as known in the art (Laemmli, Nature, 227:680-685, 1970). However, prior to denaturation of the protein samples (e.g., 10 min in SDS-containing sample buffer at 100° C.), inactivation of the protease activity was required in order to prevent auto-degradation. Protease inactivation was accomplished by incubating the protein sample with 1 mM PMSF for 30 min at room temperature or by precipitation of the protein with 8% trichloroacetic acid (TCA) for 30 min on ice. Protein samples were subjected to native PAGE carried out at pH 7.45. The gel buffer consisted of 20 mM histidine and 50 mM 3-[N-morpholino]propanesulfonic acid (MOPS), and the 5% polyacrylamide gels had a acrylamide:bisacrylamide ratio of 20:1. Protein samples were loaded on top of slab gels and electrophoresed towards the cathode. The same histidine/MOPS buffer was used as electrophoresis (tank) buffer, but adjusted to pH 6.3. Following electrophoresis (~1-2 hr at 350 V), the gel was soaked in 8% acetic acid to fix the proteins in the gel and subsequently stained with Coomassie Brilliant Blue R250 and destained as known in the art, to locate protein bands on the gel.

The protease sample purity was also confirmed by HPLC analysis using a MonoS cation exchange column followed by a TSK 2000 gel filtration column. The former was run in a 10 mM sodium phosphate buffer pH 5.5 with elution of the bound protease using a linear gradient of 10-300 mM sodium phosphate, pH 5.5. The gel filtration column was run in 0.25M sodium acetate pH 5.5. Protein elution profiles were monitored at 280 nm to locate the protease of interest and to determine the percent purity of the sample.

Example 4

Determination of the Subtilisin Concentration

In this Example, methods used to determine subtilisin concentrations are described. In some experiments extinction measurements were made at 280 nm using the calculated extinction coefficient (ϵ), and active site titrations were used to determine the protein concentration in a purified protease solution, as described below.

The extinction coefficient at 280 nm was calculated from the number of tryptophans (Trp, ϵ[epsilon]=5,600 $M^{-1}\cdot cm^{-1}$) and tyrosines (Tyr, ϵ=1,330 $M^{-1}\cdot cm^{-1}$) per enzyme molecule. For the PB92 protease the molar extinction coefficient was 26,100 $M^{-1}\cdot cm^{-1}$ (3 Trp+7 Tyr residues) equivalent to $\epsilon_{1\%}$, measured at 280 nm=9.7 ($M_r$=26,729 Da). In the case of mutants with an altered number of tryptophan and/or tyrosine residues, corrections were made accordingly.

An estimation of the concentration of active enzyme molecules was obtained by active site titration. Since the widely used method of acylation by N-transcinnamoylimidazole (Bender et al., J Am Chem Soc, 88:5890-5931, 1966) proved not to work satisfactorily for PB92 protease, a method using the irreversible inhibitor PMSF was developed instead. In this method a protease solution with an estimated enzyme concentration (from the 280 nm absorption) was mixed with 0.25, 0.50, 0.75, 1.00 and 1.25 equivalents of PMSF, respectively, and allowed to react for one hour at room temperature in 10 mM sodium phosphate pH 6.5. Residual protease activity was measured spectrophotometrically using succinyl-L-alanyl-L-alanyl-L-prolyl-L-phenyl-alanyl-para-nitroanilide (suc-AAPF-pNA) as a substrate. For these studies, the purity (and hence concentration) of PMSF was determined by NMR-spectroscopy and stock solutions of PMSF were prepared in isopropanol. The active site titration results were found to be in agreement with the protein concentration results from the purity check using the HPLC method.

Example 5

Wash Performance Tests

In this Example, methods suitable for evaluation of dishwashing and fabric cleaning performance of the subtilisin variant PX3 and the GCI-P038 reference subtilisin in commercially available dish and laundry detergents are described.

The amino acid sequence of the mature PB92 protease variant referred to herein as PX3 and having substitutions N76D+N87R+G118R+S128L+P129Q+S130A+S188D+N248R (BPN' numbering) is:

(SEQ ID NO: 5)

AQSVPWGISRVQAPAAHNRGLTGSGVKVAVLDTGISTHPDLNIRGGASFV

PGEPSTQDGNGHGTHVAGTIAALDNSIGVLGVAPRAELYAVKVLGASGSG

SVSSIAQGLEWAGNNRMHVANLSLGLQAPSATLEQAVNSATSRGVLVVAA

SGNSGAGSISYPARYANAMAVGATDQNNNRADFSQYGAGLDIVAPGVNVQ

STYPGSTYASLNGTSMATPHVAGAAALVKQKNPSWSNVQIRRHLKNTATS

LGSTNLYGSGLVNAEAATR.

The amino acid sequence of the mature GCI-P037 (PB92) reference subtilisin is:

(SEQ ID NO: 6)

AQSVPWGISRVQAPAAHNRGLTGSGVKVAVLDTGISTHPDLNIRGGASFV

PGEPSTQDGNGHGTHVAGTIAALNNSIGVLGVAPNAELYAVKVLGASGSG

SVSSIAQGLEWAGNNGMHVANLSLGSPSPSATLEQAVNSATSRGVLVVAA

SGNSGAGSISYPARYANAMAVGATDQNNNRASFSQYGAGLDIVAPGVNVQ

STYPGSTYASLNGTSMATPHVAGAAALVKQKNPSWSNVQIRNHLKNTATS

LGSTNLYGSGLVNAEAATR.

The amino acid sequence of the mature GCI-P038 reference subtilisin is:

(SEQ ID NO: 7)

AQSVPWGISRVQAPAAHNRGLTGSGVKVAVLDTGISTHPDLNIRGGASFV

PGEPSTQDGNGHGTHVAGTIAALNNSIGVLGVAPNAELYAVKVLGASGSG

SVSSIAQGLEWAGNNVMHVANLSLGLQAPSATLEQAVNSATSRGVLVVAA

SGNSGAGSISYPARYANAMAVGATDQNNNRASFSQYGAGLDIVAPGVNVQ

STYPGSTYASLNGTSMATPHVAGAAALVKQKNPSWSNVQIRNHLKNTATS

LGSTNLYGSGLVNAEAATR

Dishwashing Performance

In this example, the methods used to measure the dishwashing performance of the subtilisin variant PX3 and the GCI-P038 reference subtilisin in commercially available dish detergents are described.

The performance of the variant protease was tested under various automatic dishwashing conditions. The compositions of the dish detergents are shown in Tables 5-1 and 5-2. These detergents are commercially available from wfk Testmaterials and are referred to by their wfk Testmaterials designations. These detergents were obtained from the source without the presence of enzymes, to permit analysis of the protease variant.

TABLE 5-1

| Phosphate-Free Detergent IEC-60436 WFK Type B (pH = 10.4 in 3 g/l) | |
|---|---|
| Component | Wt % |
| Sodium citrate dehydrate | 30.0 |
| Maleic acid/Acrylic acid copolymer sodium Salt | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

TABLE 5-2

| Phosphate-Containing Detergent: IEC-60436 WFK Type C (pH = 10.5 in 3 g/l) | |
|---|---|
| Component | Wt % |
| Sodium tripolyphosphate | 23.0 |
| Sodium citrate dehydrate | 22.3 |
| Maleic acid/Acrylic acid copolymer sodium salt | 4.0 |
| Sodium perborate monohydrate | 6.0 |
| TAED | 2.0 |
| Sodium disilicate: Protil A (Cognis) | 5.0 |
| Linear fatty alcohol ethoxylate | 2.0 |
| Sodium carbonate anhydrous | add to 100 |

The protocols for preparation of each of the stain types (egg yolk, minced meat and egg, and egg with milk) are provided below. Before the individual soil types were applied to the test dishes, the dishes were thoroughly washed. This was particularly necessary, as residues of certain persistent stains may still be present on the dishes from previous tests. New dishes were also subjected to three thorough washes before being used for the first time in a test.

Preparation of Egg Yolk Stains on Stainless Steel

The stainless steel sheets (10×15 cm; brushed on one side) used in these experiments were thoroughly washed at 95° C. in a laboratory dishwasher with a high-alkalinity commercial detergent (e.g., ECOLAB® detergent; Henkel) to provide sheets that were clean and grease-free. These sheets were deburred prior to their first use. The sheets were dried for 30 minutes at 80° C. in a thermal cabinet before being soiled with egg yolk. The surfaces to be brushed were not touched prior to soiling. Also, no water stains or fluff on the surfaces were permitted. The cooled sheets were weighed before soiling.

The egg yolks were prepared by separating the yolks of approximately 10-11 eggs (200 g of egg yolk) from the whites. The yolks were stirred with a fork in a glass beaker to homogenize the yolk suspension. The yolks were then strained (approximately 0.5 mm mesh) to remove coarse particles and any egg shell fragments.

A flat brush (2.5") was used to apply 2.0±0.1 g egg yolk suspension as uniformly as possible over an area of 140 $cm^2$ on the brushed sides of each of the stainless steel sheets, leaving an approximately 1 cm wide unsoiled rim (adhesive tape was used if needed). The soiled sheets were dried horizontally (to prevent formation of droplets on the edges of the sheets), at room temperature for 4 hours (max. 24 hr).

To denaturate the egg yolk proteins, the sheets were immersed for 30 seconds in boiling, demineralized water (using a holding device if necessary). Then the sheets were dried again for 30 min at 80° C. After drying and cooling, the sheets were weighed. After weighing, the sheets were left for at least 24 hrs (20° C., 40-60% relatively humidity) before submitting them to the wash test. In order to meet the testing requirements, only sheets with 1000±100 mg/140 $cm^2$ (egg yolk after denaturation) were used in the testing. After the wash tests were conducted, the sheets were dried for 30 min at 80° C. in the thermal cabinet and weighed again after cooling. The percent cleaning performance was determined by dividing the mg of egg yolk released upon washing by the mg of denatured egg yolk applied and multiplying by 100.

Preparation of Minced Meat and Egg Stains on Porcelain Plates

For these experiments, dessert plates (Arzberg, 19 cm diameter, white, glazed porcelain) conforming to EN 50242, form 1495, No. 0219, were used. A total of 225 g lean pork and beef (50:50 ratio) was finely chopped and maintained cool. The mixture was twice run through a mincer. Temperatures above 35° C. were avoided. The 225 g of the minced meat was then mixed with 75 g of egg (white and yolk mixed together). The preparation was then frozen for up to three months at −18° C., prior to use. If pork was not available, 100% beef was used, as these are interchangeable.

The minced meat and egg mixture (300 g) was brought to room temperature and mixed with 80 ml demineralized water. The mixture was then homogenized for 2 min using a kitchen hand blender. A fork was used to spread 3 g of the minced meat/egg/water mixture on each white porcelain plate, leaving an approximately 2 cm wide unsoiled margin around the rim. The amount applied was 11.8±0.5 mg/$cm^2$. The plates were dried for 2 hours at 120° C. in a preheated thermal cabinet. As soon as the plates were cooled, they were ready for use.

After conducting the dishwashing tests, the plates were sprayed with ninhydrin solution (prepared to 1% in ethanol) for better identification of the minced meat protein residues. To promote the color reaction, the plates were heated for 10 min at 80° C. in the thermal cabinet. Evaluation of the washing performance was done by visually inspecting the color reactions of the minced meat residue with reference to the IKW photographic catalogue (IKW—The German Cosmetic, Toiletry, Perfumery and Detergent Association).

Preparation of Egg/Milk Stains on Stainless Steel

The stainless steel sheets (10×15 cm; brushed on one side) used in these experiments were thoroughly washed at 95° C. in a laboratory dishwasher with a high-alkalinity commercial detergent to remove grease and clean the sheets. The sheets were polished dry with a cellulose cloth. The surfaces to be brushed were not touched prior to soiling. Also, no water stains or fluff on the surfaces were permitted. Before soiling, the sheets were placed in a thermal cabinet at 80° C., for 30 min. The cooled sheets were weighed before soiling.

The egg yolks and whites of whole raw eggs (3-4 eggs; approximately 160 g/egg) were placed in a bowl and beaten with an egg whisk. Then, 50 ml semi-skimmed milk (1.5% fat, ultra-high-temperature, homogenized) were added to the mixture. The milk and egg were mixed without generating froth. A flat brush was used to uniformly distribute 1.0±0.1 g of the egg/milk mixture on the brushed side of the stainless steel sheets, using a balance to check the distribution. A margin of approximately 1.0 cm was left around the short sides of the sheets. The soiled sheets were dried horizontally (to prevent formation of droplets on the edges of the sheets), at room temperature for 4 hours (max. 24 hr).

The sheets were then immersed for 30 seconds in boiling, demineralized water (using a holding device if necessary). Then the sheets were dried again for 30 min at 80° C. After drying and cooling the sheets were weighed. After weighing the sheets were left to sit for at least 24 hours (20° C., 40-60% relatively humidity) before submitting them to the wash test.

In order to meet the testing requirements, only sheets with 190±10 mg egg yolk/milk were used.

After the wash tests were conducted, the sheets were dried for 30 min at 80° C., in the thermal cabinet, and weighed again after cooling. The percentage cleaning performance was determined by dividing the mg of egg/milk released upon washing by the mg of egg/milk applied and multiplying by 100.

Washing Equipment and Conditions

The washing tests were performed in an automatic dishwasher (Miele model G690SC), equipped with soiled dishes and stainless steel sheets, prepared as described above. A defined amount of the detergent was used. The temperature tested was 50° C. The water hardness was 21° GH (German hardness).

As described above, after washing the plates soiled with minced meat were visually assessed using a photo rating scale of 0 to 10, wherein "0" designated a completely dirty plate and "10" designated a clean plate. These values correspond to the stain or soil removal (SR) capability of the enzyme-containing detergent.

The washed stainless steel plates soiled with egg yolk or egg yolk/milk were analyzed gravimetrically to determine the amount of residual stain after washing. The subtilisin variant PX3 and the GCI-P038 reference subtilisin were tested at a level of between 0 and 30 mg/active protein per wash.

The results for various dishwashing tests are provided below in Tables 5-3 to 5-6. In each of these experiments, different concentrations of active protease per wash were used. The wash performance of the GCI-P038 reference subtilisin was assigned a value of "100," while the wash performance of the variant was compared to this value. For example, if the GCI-P038 reference subtilisin had a result of 45% stain removal and a variant had a result of 52% stain removal, the result for the subtilisin variant shown as a performance index (PI) would be 52/45×100=116. Thus in both detergents tested, the subtilisin variant PX3 was more or as effective as the GCI-P038 reference subtilisin in removing proteinaceous stains in dishwashing applications.

TABLE 5-3

| Phosphate-Containing Detergent, 50° C., 21° GH, dosed at 0.05% active protein | | | |
|---|---|---|---|
| Enzyme | PI Egg Yolk | PI Minced Meat | PI Egg Yolk/Milk |
| Reference GCI-P038 | 100 | 100 | 100 |
| Variant PX3 | 111 | 157 | 147 |

TABLE 5-4

| Phosphate-Containing Detergent 50° C., 21° GH, dosed at 0.15% active protein | | | |
|---|---|---|---|
| Enzyme | PI Egg Yolk | PI Minced Meat | PI Egg Yolk/Milk |
| Reference GCI-P038 | 100 | 100 | 100 |
| Variant PX3 | 135 | 100* | 113 |

*Under these specified conditions soil removal was 100%.

TABLE 5-5

| Phosphate-Free Detergent 50° C., 21° GH, dosed at 0.05% active protein | | | |
|---|---|---|---|
| Enzyme | PI Egg Yolk | PI Minced Meat | PI Egg Yolk/Milk |
| Reference GCI-P038 | 100 | 100 | 100 |
| Variant PX3 | 124 | 150 | 117 |

TABLE 5-6

| Phosphate-Free Detergent 50° C., 21° GH, dosed at 0.15% active protein | | | |
|---|---|---|---|
| Enzyme | PI Egg Yolk | PI Minced Meat | PI Egg Yolk/Milk |
| Reference GCI-P038 | 100 | 100 | 100 |
| Variant PX3 | 115 | 118 | 103 |

Example 6

Stability and Cleaning Performance of Subtilisin Variant

In this Example, methods to assess the stability and cleaning performance of PX3 are described.

AAPF Hydrolysis Assay Method

The thermostability of the serine protease variant was determined by assaying protease activity using the AAPF assay after incubation of protease variant at 68° C. for 1 hour. Under the conditions of the assay, the residual activity of the reference protease (e.g., wild type GG36=GCI-P036) was about 50%. The equipment used was: F-bottom MTPs (Costar No. 9017), Biomek FX and/or Biomek FXp Robot (Beckman Coulter), Spectramax Plus 384 MTP Reader (Molecular Devices), iEMS Incubator/Shaker (1 mm amplitude) (Thermo/Labsystems), Sealing tape (Nunc No. 236366), and ice bath. Glycine buffer was prepared by dissolving 3.75 g glycine (Merck No. 1.04201.1000) in 960 mL water. 1 ml of 5% TWEEN®-80 (Sigma No. P-8074) and 10 ml of a stock solution of 1000 mM $CaCl_2$ (Merck No. 1.02382.1000) (29.4 g dissolved to 200 ml) was added to this solution. The pH was adjusted to 10.5 with 4N NaOH and the volume brought up to 1000 ml. Final concentrations of glycine, $CaCl_2$ and TWEEN®-80 were: 50 mM, 10 mM and 0.005% respectively. The incubators were set at 68° C. (for incubation) and at 25° C. (for the AAPF assay). 90 μl and 190 μl glycine buffer was added to the empty dilution and incubation plates respectively. 10 μl of supernatant was then added to the dilution plate, followed by addition of 10 μl from the dilution plate to the incubation plate. Then 10 μl of mixture from the incubation plate was added to a pre-warmed plate containing suc-AAPF-pNA substrate. The suc-AAPF-pNA plate was read in MTP Reader at 410 nm (t=0 measurement). The incubation plate was covered with tape and incubated for 1 hour at 68° C. and 400 rpm. At the end of the incubation, the plate was removed from the incubator and cooled down on ice for at least 5 minutes. 10 μl of mixture from the incubation plate was transferred to the plate containing suc-AAPF-pNA substrate and the plate read at 410 nm (t=60 measurement). Percent residual activity was calculated as:

$$\%\text{residual activity:}(\text{mOD}\cdot\text{min}-1 \text{ at } t=60)/(\text{mOD}\cdot\text{min}-1 \text{ at } t=0)\times 100$$

LAS/EDTA Stability Assay

LAS/EDTA stability was measured after incubation of the test protease in the presence of LAS/EDTA, as a function of residual activity determined using the AAPF assay.

The stability of the protease variant and control protease in the presence of a representative anionic surfactant (LAS=linear alkylbene sulfonate, sodium dodecylbenzenesulfonate-DOBS) and di-sodium EDTA was measured after incubation under defined conditions and the residual activity was determined using the AAPF assay. The reagents used were dodecyllbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstress buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 μg/ml protein. The equipment used was V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), iEMS Incubator/Shaker (1 mm amplitude) from Thermo Electron Corporation, sealing tape: Nunc (236366).

The iEMS incubator/shaker (Thermo/Labsystems) was set at 29° C. Culture supernatants were diluted into plates containing unstress buffer to a concentration of ~25 ppm (master dilution plate). 20 μl of sample from the master dilution plate was added to plates containing 180 μl unstress buffer to give a final incubation concentration of 2.5 ppm. The contents were mixed and kept at room temperature and a AAPF assay was performed on this plate. 20 μl of sample from the master dilution plate was also added to plates containing 180 μl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 mM at 400 rpm. Following 30 minutes of incubation, an AAPF assay was performed on the stress plate. The stability of the samples was determined by calculating the ration of the residual and initial AAPF activity as follows: Residual Activity (%)=[mOD·min−1 stressed]*100/[mOD·min−1 unstressed].

Baked Egg Yolk Microswatch Assay

The stain removal performance of the subtilisin variant was determined on a microtiter plate (MTP) scale in commercially available detergents (CALGONIT® detergent [Reckitt-Benckiser]; and CASCADE® detergent [P&G]). Samples for testing the subtilisin variant were obtained from filtered culture broth of cultures grown in MTP plates for 3 days at 37° C./300 rpm/90% relative humidity. The equipment used included: a Biomek FX Robot (Beckman Coulter), a SpectraMAX MTP Reader (type 340; Molecular Devices), an iEMS incubator/shaker (Thermo/Labsystems); F-bottom MTPs (Costar type 9017) for reading of reaction plates after incubation and V-bottom MTPs (Greiner 651101) for pre-dilution of supernatant. CS-38 microswatches (egg-yolk with pigment, aged by heating), obtained from CFT Vlaardingen were used as substrate. Two swatches were used per well. ADW tablets from Calgonit 5 in 1 were used to prepare the detergent solution. To inactivate the protease activity present in the tablets, a 21 g tablet was dissolved in Milli-Q water heated in a water bath to a temperature of 60° C. The solution was cooled to room temperature and the volume of water adjusted to 700 mL. The solution was further diluted with water to achieve a final concentration of 3 g/l. Water hardness was adjusted to 21° GH by adding 1.46 ml of the Ca/Mg-mixture (Ca/Mg mixture [(3:1), 1.92 M $CaCl_2$=282.3 g/L $CaCl_2.2H_2O$; 0.64 M $MgCl_2$=130.1 g/L $MgCl_2.6H_2O$), 15000 gpg]. The enzyme samples were prediluted in 10 mM NaCl, 0.1 mM $CaCl_2$, 0.005% TWEEN®-80 solution and tested at appropriate concentrations.

The incubator was set at the desired temperature of 40° C. or 50° C., and 72 μl of dilution buffer was added to the empty V-bottom plate (=dilution plate) followed by 8 μl supernatant. Then 9 μl from the dilution plate was added to plates containing the microswatches incubated in 171 μl detergent solution. The microswatch plate (with detergent and enzyme) was covered with tape and placed in the incubator/shaker for 30 minutes at 1400 rpm. Following incubation, 75 μl of the reaction mixture was transferred to an empty F-bottom plate and the absorbance was read in a MTP Reader at 405 nm after de-bubbling with a hair dryer. Blank controls, containing one or two microswatches and detergent without the addition of the reference subtilisin containing samples were also included in the test.

TABLE 6-1

| Laundry and Dish Washing Conditions | | | | | | | |
|---|---|---|---|---|---|---|---|
| Region | Form | Dose | Detergent* | Buffer | Gpg | pH | T (° C.) |
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIELl ™ | 2 mM $Na_2$ $CO_3$ | 12 | 10.5 | 40 |
| JPN | HDG | 0.7 g/L | P&G TIDE ® | 2 mM $Na_2$ $CO_3$ | 6 | 10.0 | 20 |
| NA | HDG | 1.0 g/L | P&G TIDE ® | 2 mM $Na_2$ $CO_3$ | 6 | 10.0 | 20 |
| Automatic Dish Washing | | | | | | | |
| WE | ADW | 3.0 g/L | RB CALGONIT ™ | 2 mM $Na_2$ $CO_3$ | 21 | 10.0 | 40 |
| NA | ADW | 3.0 g/L | P&G CASCADE ™ | 2 mM $Na_2$ $CO_3$ | 9 | 10.0 | 40 |

*Abbreviations: Procter & Gamble (P&G); and Reckitt Benckiser (RB).

Blood Milk Ink (BMI) Microswatch Assay

The stain removal performance of the subtilisin variant was determined on a microtiter plate (MTP) scale in commercially available detergents. Samples of the reference subtilisin and the subtilisin variant were obtained from filtered culture broth of cultures grown in MTP plates for 3 days at 37° C./300 rpm/90% relative humidity. The equipment used included: 96 well polystyrene plates (Costar No. 9017 medium binding flat bottom), Biomek FX and/or Biomek FXp (Beckman Coulter), Spectramax Plus 384 (Molecular Devices), iEMS Incubator/Shaker with 1 mm amplitude (Thermo Electron Corporation) and sealing tape (Nunc No.

236366). The reagents used include: 5 mM HEPES, pH 8.0 or 5 mM MOPS, pH 7 buffer, 3:1 Ca: Mg for medium water hardness. (CaCl2: MgCl2.6H2O); 15000 grains per gallon (gpg) stock diluted to 6 gpg, two BMI (blood/milk/ink) swatches per plate: EMPA-116 BMI cotton swatches processed by CFT: pre-rinsed and punched two swatches per well, and heat inactivated TIDE® 2X off-the-shelf detergent in which lack of protease activity was confirmed. In this assay, the proteases hydrolyze the substrate and liberate pigment and insoluble particles from the substrate.

TABLE 6-2

| Working Detergent Solutions | | | | | |
|---|---|---|---|---|---|
| Detergent | Temp (° C.) | Detergent g/L | pH | Buffer | gpg |
| TIDE ® 2X | 16 | 0.98 | 8 | 5 mM HEPES | 6 |
| TIDE ® 2X | 32 | 0.98 | 8 | 5 mM HEPES | 6 |
| TIDE ® 2X | 16 | 0.98 | 7 | 5 mM MOPS | 6 |

The incubator was set at the desired temperature (16° C. or 32° C.). First, 10 μL samples from the master dilution plate of ~10 ppm enzyme were added to BMI 2-swatch plates with 190 μL working detergent solutions listed above. The volume was adjusted to give final concentration of 0.5 ppm for variant in the assay plates. The plates were then immediately transferred to iEMS incubators and incubated for 30 minutes with 1400 rpm shaking at given temperature. Following incubation, 100 μL of supernatant was transferred into a new 96-well plate and the absorbance was measured in MTP Reader at 405 nm and/or 600 nm. Control wells, containing one or two microswatches and detergent without the addition of protease samples were also included in the test. The measurement at 405 nm provides a higher value and tracks pigment removal, while the measurement at 600 nm tracks turbidity and cleaning.

Calculation of the Stain Removal Activity

The absorbance value obtained was corrected for the blank value (substrate without enzyme), providing a measure of hydrolytic activity. For each sample (variant) the performance index (PI) was calculated. The performance index compares the performance of the variant (actual value) and the reference enzyme (theoretical value) at the same protein concentration. In addition, the theoretical values can be calculated, using the parameters of the Langmuir equation of the standard enzyme. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

The cleaning performance of the subtilisin variant was determined using a microswatch assay (CS-38 swatches). The LAS/EDTA stability and thermostability for the variant was also determined using methods described above. Results are shown in Table 6-3.

TABLE 6-3

$P_i$ Values for PX3 Tested for Stain Removal Performance on CS-38 Swatches, LAS/EDTA Stability and Thermostability

| Variant | Variant Substitutions Based on GCI-P036 | CALGON* 5 in 1 40° C. | CALGON* 5 in 1 50° C. | CASC** Complete 50° C. | LAS-EDTA Stability | Thermo-stability |
|---|---|---|---|---|---|---|
| PX3 | S87R/G118R/S128L/P129Q/S130A/N76D/S188D/N248R | 0.93 | 1.20 | 1.24 | 1.54 | 0.7 |

*CALGONIT ® detergent;
**CASCADE ® detergent

In addition to these experiments, experiments to determine cleaning performance in laundry applications of the protease variant are provided. The test detergents are heat inactivated commercially obtained laundry detergents (e.g., TIDE® 2× Free [P&G; “NA HDL”] TIDE® Free [P&G; “NA HDD”]). Cleaning performance of BMI stained microswatches is tested using 0.2 ppm of the variant at 25° C. for 30 minutes with 1400 rpm shaking in a volume of 200 uL. Functionality of the variant is quantified as a performance index (Pi), which is the ratio of performance of a variant to a parent GCI-P036 protein.

Example 7

Liquid Laundry Detergent Compositions

In this Example, various formulations for liquid laundry detergent compositions are provided. The following liquid laundry detergent compositions of the present invention are prepared as shown below. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | |
|---|---|---|---|---|---|
| Compound | I | II | III | IV | V |
| LAS | 24.0 | 32.0 | 6.0 | 3.0 | 6.0 |
| $NaC_{16}$-$C_{17}$ HSAS | — | — | — | 5.0 | — |
| $C_{12}$-$C_{15}$ $AE_{1.8}S$ | — | — | 8.0 | 7.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | — | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 2.0 | 3.0 |
| Citric acid (anhydrous) | 4.5 | 5.0 | 3.0 | 2.0 | 1.0 |

-continued

| Compound | Formulations I | II | III | IV | V |
|---|---|---|---|---|---|
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1 N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | | — |
| Cellulase | — | — | 0.0002 | | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

#1: Add 1N HCl aq. soln to adjust the neat pH of the formula in the range from about 3 to about 5.
The pH of Examples above 7(I)-(II) is about 5 to about 7, and of 7(III)-(V) is about 7.5 to about 8.5.

Example 8

Hand Dish Liquid Detergent Compositions

In this Example, various hand dish liquid detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

| Compound | Formulations I | II | III | IV | V | VI |
|---|---|---|---|---|---|---|
| $C_{12}$-$C_{15}$ $AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 8(I)-(VI) is about 8 to about 11.

Example 9

Liquid Automatic Dishwashing Detergent Compositions

In this Example, various liquid automatic dishwashing detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

| Compound | Formulations I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 10

Granular and/or Tablet Laundry Compositions

This Example provides various formulations for granular and/or tablet laundry detergents. The following laundry compositions of present invention, which may be in the form of granules or tablet, are provided below. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | |
|---|---|---|---|---|---|
| Compound | I | II | III | IV | V |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate $2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |

-continued

| | Formulations | | | | |
|---|---|---|---|---|---|
| Compound | I | II | III | IV | V |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/$MgSO_4$/PVPVI/suds suppressor/high molecular PEG/clay.

Example 11

Liquid Laundry Detergents

This Example provides various formulations for liquid laundry detergents. The following liquid laundry detergent formulations of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | | |
|---|---|---|---|---|---|---|
| Compound | I | I | II | III | IV | V |
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | | — | — |
| Aldose Oxidase | 0.05 | — | — | 0.05 | — | 0.02 |
| Galactose oxidase | — | 0.04 | | | | |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 12

High Density Dishwashing Detergents

This Example provides various formulations for high density dishwashing detergents. The following compact high density dishwashing detergents of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | | |
|---|---|---|---|---|---|---|
| Compound | I | II | III | IV | V | VI |
| STPP | — | 45.0 | 45.0 | — | — | 40.0 |
| 3Na Citrate $2H_2O$ | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/$MgSO_4$/PVPVI/suds suppressor/high molecular PEG/clay.

The pH of Examples 12(I) through (VI) is from about 9.6 to about 11.3.

Example 13

Tablet Detergent Compositions

This Example provides various tablet detergent formulations. The following tablet detergent compositions of the present invention are prepared by compression of a granular dishwashing detergent composition at a pressure of 13 KN/cm$^2$ using a standard 12 head rotary press. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | | | | |
|---|---|---|---|---|---|---|---|---|
| Compound | I | II | III | IV | V | VI | VII | VIII |
| STPP | — | 48.8 | 44.7 | 38.2 | — | 42.4 | 46.1 | 46.0 |
| 3Na Citrate $2H_2O$ | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/$MgSO_4$/PVPVI/suds suppressor/high molecular PEG/clay.

The pH of Examples 13(I) through 13(VII) is from about 10 to about 11.5; pH of 13(VIII) is from 8-10. The tablet weight of Examples 13(I) through 13(VIII) is from about 20 grams to about 30 grams.

Example 14

Liquid Hard Surface Cleaning Detergents

This Example provides various formulations for liquid hard surface cleaning detergents. The following liquid hard surface cleaning detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

| | Formulations | | | | | | |
|---|---|---|---|---|---|---|---|
| Compound | I | II | III | IV | V | VI | VII |
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 14(I) through (VII) is from about 7.4 to about 9.5.

All patents and publications mentioned in the specification are indicative of the levels of those skilled in the art to which the invention pertains. Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not excised material is specifically recited herein.

We claim:

1. A subtilisin variant comprising the amino acid sequence set forth in SEQ ID NO:5.

2. A composition comprising the subtilisin variant of claim 1.

3. The composition of claim 2, wherein said composition is a cleaning composition.

4. The cleaning composition of claim 3, wherein said composition is a laundry detergent.

5. The cleaning composition of claim 3, wherein said composition is a dishwashing detergent.

6. The dishwashing detergent of claim 5, wherein said dishwashing detergent is an automatic dishwashing detergent.

7. The cleaning composition of claim 3, wherein said composition is a liquid detergent.

8. The cleaning composition of claim 3, wherein said composition is a gel, tablet, powder or granule detergent.

9. The cleaning composition of claim 3, wherein said composition does not contain phosphate.

10. The cleaning composition of claim 3, further comprising at least one bleaching agent.

11. The cleaning composition of claim 4, further comprising at least one bleaching agent.

12. The cleaning composition of claim 5, further comprising at least one bleaching agent.

13. The cleaning composition of claim 3, further comprising at least one additional enzyme.

14. The cleaning composition of claim 13, wherein said at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

15. The cleaning composition of claim 4, further comprising at least one additional enzyme.

16. The cleaning composition of claim 13, wherein said at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

17. The cleaning composition of claim 5, further comprising at least one additional enzyme.

18. The cleaning composition of claim 17, wherein said at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

19. A method for cleaning comprising providing an item to be cleaned and a composition comprising the subtilisin variant set forth in SEQ ID NO:5, and contacting said item with said composition.

20. The method of claim 19, further comprising the step of rinsing said item to be cleaned.

21. The method of claim 19, wherein said item is a dishware or fabric item.

22. The method of claim 21, wherein further comprising the step of rinsing the dishware or fabric item.

* * * * *

UNITED STATES PATENT AND TRADEMARK OFFICE

CERTIFICATE OF CORRECTION

PATENT NO. : 8,183,024 B2
APPLICATION NO. : 12/616106
DATED : May 22, 2012
INVENTOR(S) : Luis G. Cascao-Pereira It is certified that error appears in the above-identified patent and that said Letters Patent is hereby corrected as shown below:

On the Title page of the Letters Patent, under Inventors field code (75), please delete the word "Poulise" and insert the word -- Poulose --.

Signed and Sealed this
Twentieth Day of November, 2012

David J. Kappos
*Director of the United States Patent and Trademark Office*

SEQUENCE LISTING

<160> NUMBER OF SEQ ID NOS: 7

<210> SEQ ID NO 1
<211> LENGTH: 38
<212> TYPE: DNA
<213> ORGANISM: Artificial Sequence
<220> FEATURE:
<223> OTHER INFORMATION: Synthetic primer: N76D-Fw

<400> SEQUENCE: 1
cgggacgatt gctgctttag acaattcgat tggcgttc 38

<210> SEQ ID NO 2
<211> LENGTH: 38
<212> TYPE: DNA
<213> ORGANISM: Artificial Sequence
<220> FEATURE:
<223> OTHER INFORMATION: Synthetic primer: N76D-Rv

<400> SEQUENCE: 2
gaacgccaat cgaattgtct aaagcagcaa tcgtcccg 38

<210> SEQ ID NO 3
<211> LENGTH: 30
<212> TYPE: DNA
<213> ORGANISM: Artificial Sequence
<220> FEATURE:
<223> OTHER INFORMATION: Synthetic primer: pHPLT-BglII-Fw

<400> SEQUENCE: 3
gcaattcaga tcttccttca ggttatgacc 30

<210> SEQ ID NO 4
<211> LENGTH: 30
<212> TYPE: DNA
<213> ORGANISM: Artificial Sequence
<220> FEATURE:
<223> OTHER INFORMATION: Synthetic primer: pHPLT-BglII-Rv

<400> SEQUENCE: 4
gcatcgaaga tctgattgct taactgcttc 30

<210> SEQ ID NO 5
<211> LENGTH: 269
<212> TYPE: PRT
<213> ORGANISM: Artificial Sequence
<220> FEATURE:
<223> OTHER INFORMATION: Chemically synthesized protease variant

<400> SEQUENCE: 5

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Arg Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Arg Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Asp Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Arg His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 6
<211> LENGTH: 269
<212> TYPE: PRT
<213> ORGANISM: Bacillus sp.

<400> SEQUENCE: 6

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
```

```
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 7
<211> LENGTH: 269
<212> TYPE: PRT
<213> ORGANISM: Bacillus sp.

<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
```

-continued

```
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```